A61F 2013/8497 (2013.01)

(12) United States Patent (10) Patent No.: US 11,096,842 B2
Michielsen et al. (45) Date of Patent: Aug. 24, 2021

(54) CLOSURE ASSEMBLIES USING EXTENDED FINGERLIFTS

(71) Applicant: Avery Dennison Corporation, Glendale, CA (US)

(72) Inventors: Loes Michielsen, Hoogstraten (BE); Johan Van Steen, Ravels (BE)

(73) Assignee: Avery Dennison Corporation, Glendale, CA (US)

( * ) Notice: Subject to any disclaimer, the term of this patent is extended or adjusted under 35 U.S.C. 154(b) by 791 days.

(21) Appl. No.: 15/309,923

(22) PCT Filed: May 21, 2015

(86) PCT No.: PCT/US2015/031994
§ 371 (c)(1),
(2) Date: Nov. 9, 2016

(87) PCT Pub. No.: WO2015/179655
PCT Pub. Date: Nov. 26, 2015

(65) Prior Publication Data
US 2017/0266066 A1 Sep. 21, 2017

Related U.S. Application Data

(60) Provisional application No. 62/001,794, filed on May 22, 2014.

(51) Int. Cl.
*A61F 13/15* (2006.01)
*A61F 13/60* (2006.01)
*A61F 13/56* (2006.01)
*A61F 13/84* (2006.01)

(52) U.S. Cl.
CPC .......... *A61F 13/60* (2013.01); *A61F 13/5622* (2013.01); *A61F 13/5633* (2013.01); *A61F 13/84* (2013.01); *A61F 2013/5666* (2013.01); *A61F 2013/8497* (2013.01)

(58) Field of Classification Search
CPC .. A61F 13/60; A61F 13/5622; A61F 13/5633; A61F 13/84; A61F 2013/5666; A61F 2013/8497
USPC ........ 604/389, 386, 387, 390, 391, 394, 396
See application file for complete search history.

(56) References Cited

U.S. PATENT DOCUMENTS

| 4,552,560 A | 11/1985 | Tritsch |
| 5,026,446 A * | 6/1991 | Johnston ........... A61F 13/15601 156/153 |
| 5,288,546 A * | 2/1994 | Roessler ................. A61F 13/58 428/40.1 |
| 5,510,161 A | 4/1996 | Lloyd |

(Continued)

FOREIGN PATENT DOCUMENTS

| EP | 0581323 | 2/1994 |
| EP | 0941729 | 9/1999 |

(Continued)

OTHER PUBLICATIONS

International Search Report and Written Opinion issued in corresponding IA No. PCT/US2015/031994 dated Sep. 11, 2015.

(Continued)

*Primary Examiner* — Jacqueline F Stephens

(57) ABSTRACT

Extended fingerlifts and their use in closure assemblies typically provided in absorbent articles such as diapers are described.

19 Claims, 5 Drawing Sheets

FIG. 1A

(56) References Cited

U.S. PATENT DOCUMENTS

| | | | | |
|---|---|---|---|---|
| 5,549,592 | A | * | 8/1996 | Fries ................ A61F 13/58 |
| | | | | 604/389 |
| 5,599,601 | A | | 2/1997 | Polski et al. |
| 5,611,789 | A | | 3/1997 | Seth |
| 5,624,429 | A | * | 4/1997 | Long ............. A61F 13/5622 |
| | | | | 604/391 |
| 6,210,389 | B1 | * | 4/2001 | Long ............ A44B 18/0069 |
| | | | | 24/442 |
| 6,463,633 | B1 | | 10/2002 | Sangani et al. |
| 2001/0023341 | A1 | | 9/2001 | Karami |
| 2002/0147437 | A1 | | 10/2002 | McLaughlin et al. |
| 2003/0008106 | A1 | | 1/2003 | Guenther et al. |
| 2005/0277905 | A1 | | 12/2005 | Pedersen et al. |
| 2011/0004182 | A1 | | 1/2011 | Hilston et al. |
| 2014/0010984 | A1 | | 1/2014 | Bogaerts et al. |

FOREIGN PATENT DOCUMENTS

| | | |
|---|---|---|
| EP | 1762207 | 3/2007 |
| EP | 1878413 | 1/2008 |
| EP | 2255769 | 12/2010 |
| WO | 2006/138016 | 12/2006 |
| WO | 2007/059933 | 5/2007 |
| WO | 2013/160170 | 10/2013 |

OTHER PUBLICATIONS

International Preliminary Report on Patentability issued in corresponding IA No. PCT/US2015/031994 dated Nov. 22, 2015.

* cited by examiner

CLOSURE ASSEMBLIES USING EXTENDED FINGERLIFTS

CROSS-REFERENCE TO RELATED APPLICATION

The present application is a 371 of International Application No. PCT/US15/31994, which was published in English on Nov. 26, 2015, and claims the benefit of U.S. Provisional Patent Application No. 62/001,794 filed May 22, 2014, both of which are incorporated herein by reference in their entireties.

FIELD

The present subject matter relates to closure assemblies such as used in absorbent articles for example diapers. The closure assemblies include extended fingerlifts that promote identification and grasping of a fastening member of the closure assembly.

BACKGROUND

Personal care absorbent articles such as diapers typically include one or more closure assemblies which enable selective positioning of the article. Closure assemblies may include adhesive or mechanical closure elements such as Velcro, or combinations thereof. Generally, closure assemblies include a thin flexible fastening member or strip which is incorporated in the article. An end of the strip is typically accessible for grasping by a user.

To facilitate identification and thus grasping and use of closure assemblies, it is known to apply inks or other markings along an end of a strip of a closure assembly. However, inks or other printed materials are susceptible to removal upon exposure to wear, rubbing, and liquids as may be encountered during use of an absorbent article. In addition for certain applications such as the hygienic consumer market, safety issues may arise with regard to such nonadherent inks.

Instead of printing inks on strips of closure assemblies, it is also known to laminate a section of a thin material to the end of such strips. The section of material may be colored or otherwise visually pronounced to thus facilitate identification by a user. Such visually pronounced sections of material are laminated along an underside of a closure strip, which typically contains adhesive. Although satisfactory in certain respects, attachment of such sections along the underside of a closure strip often obscures recognition of the strip since the section is covered by the strip. Lamination of the section along an opposite face of a closure strip is generally undesirable because such face is typically release coated thus discouraging any bonding thereto. Haphazard bonding between sections of materials and closure strips is unacceptable due to resulting safety issues and perceptions of poor quality. Use of closure assembly strips which are free of release coating in certain designated regions would in theory be possible in order that the visually pronounced section of material be laminated to the region(s) free of release coating. However, this strategy would involve pattern coating of release material and increase manufacturing complexity and thus cost.

In view of these and other factors, a need exists for a strategy to economically and reliably secure a visually pronounced section of material to a closure assembly strip which avoids the noted concerns.

SUMMARY

The difficulties and drawbacks associated with previous approaches are addressed in the present subject matter as follows.

In one aspect, the present subject matter provides an extended fingerlift configured for securement at a distal end of a carrier strip of a closure assembly. The extended fingerlift comprises an extension strip defining a proximal end, a distal end, an outer face and an oppositely directed underside. The extended fingerlift also comprises a fingerlift strip defining a proximal end, a distal end, an outer face and an oppositely directed underside. The extension strip and the fingerlift strip are positioned relative to one another to thereby define a receiving region for receipt of the distal end of the carrier strip.

In another aspect, the present subject matter provides a closure assembly configured for incorporation and use in an absorbent article. The closure assembly comprises a fastening tape carrier defining a proximal end, a distal end, an outer face, and an oppositely directed underside. The closure assembly also comprises an extended fingerlift including (i) an extension strip defining a proximal end, a distal end, an outer face and an oppositely directed underside, and (ii) a fingerlift strip defining a proximal end, a distal end, an outer face and an oppositely directed underside. The extension strip and the fingerlift strip are positioned relative to one another to thereby define a receiving region for receipt of the distal end of the carrier strip. The closure assembly also comprises provisions for securing the extended fingerlift to the distal end of the carrier strip upon receipt of the distal end of the carrier strip in the receiving region defined by the extended fingerlift. The closure assembly is configured such that the distal end of the fastening tape carrier is received and secured in the receiving region defined by the extended fingerlift.

In still another aspect, the present subject matter provides a closure assembly configured for incorporation and use in an absorbent article. The closure assembly comprises a fastening tape carrier defining a proximal end and an opposite distal end. The closure assembly also comprises an extension member attached to the fastening tape carrier and extending outward beyond the distal end of the fastening tape carrier. The extension member and the fastening tape carrier define (i) a dimension of overlap and (ii) a dimension of extension. The ratio of (ii) to (i) is within a range of from 50:1 to 3:1.

In yet another aspect, the present subject matter provides a method of facilitating identification and grasping of a fastening member of a closure assembly of an absorbent article. The method comprises providing a closure assembly of an absorbent article. The closure assembly includes a fastening tape carrier defining a proximal end, a distal end, an outer face, and an oppositely directed underside. The method also comprises providing an extended fingerlift including (i) an extension strip defining a proximal end, a distal end, an outer face and an oppositely directed underside, and (ii) a fingerlift strip defining a proximal end, a distal end, an outer face and an oppositely directed underside. The extension strip and the fingerlift strip are positioned relative to one another to thereby define a receiving region for receipt of the distal end of the fastening tape carrier. The method also comprises positioning the distal end of the fastening tape carrier in the receiving region defined by the extended fingerlift. And, the method additionally comprises securing the extended fingerlift to the distal end of the fastening tape carrier.

As will be realized, the subject matter described herein is capable of other and different embodiments and its several details are capable of modifications in various respects, all without departing from the claimed subject matter. Accordingly, the drawings and description are to be regarded as illustrative and not restrictive.

DETAILED DESCRIPTION OF THE EMBODIMENTS

The present subject matter provides extended fingerlifts and closure assemblies using such extended fingerlifts. The present subject matter also provides absorbent articles including such closure assemblies. And, the subject matter provides various methods of use. The closure assemblies can be used in a wide array of personal care absorbent articles such as diapers and feminine hygiene articles. The extended fingerlifts comprise (i) a thin extension strip, (ii) a fingerlift strip adjoined or laminated to the extension strip, and in certain embodiments also comprise (iii) provisions for securing (i) and/or (ii) to a distal end of a fastening tape carrier such as typically used in closure assemblies for personal care absorbent articles. Details of each of these components, materials of construction, methods of producing and using, and additional aspects are all described herein.

Figure 1:
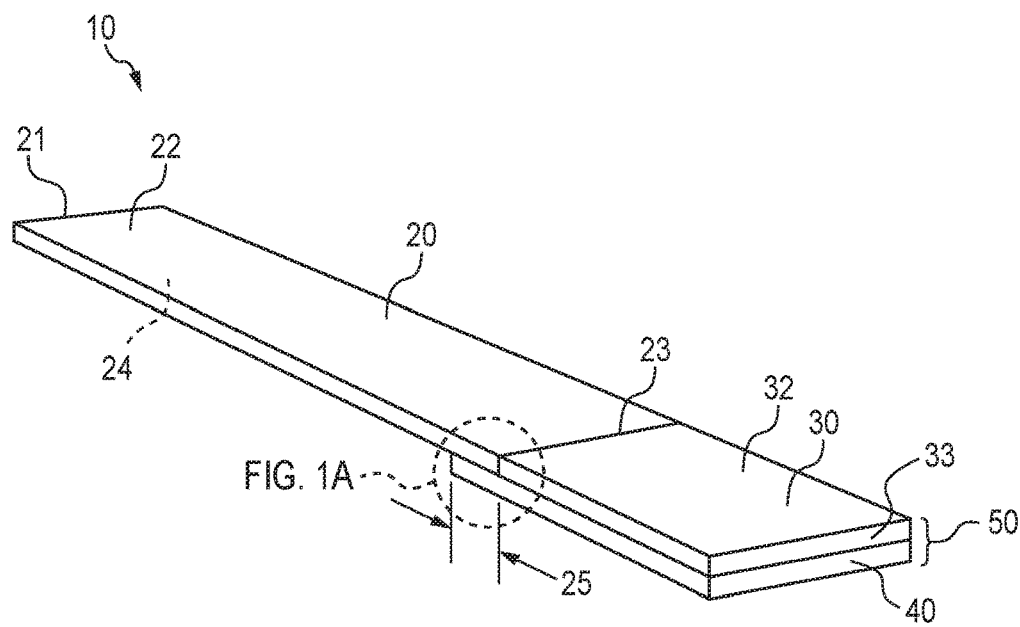
FIG. 1 is a schematic perspective view of an embodiment of a closure assembly including an extended fingerlift in accordance with the present subject matter.
Figure 1A:
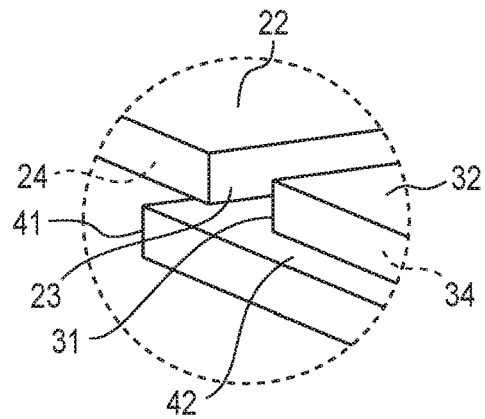
FIG. 1A is a detailed, partially exploded view illustrating a particular configuration of components in the closure assembly.
Figure 2:
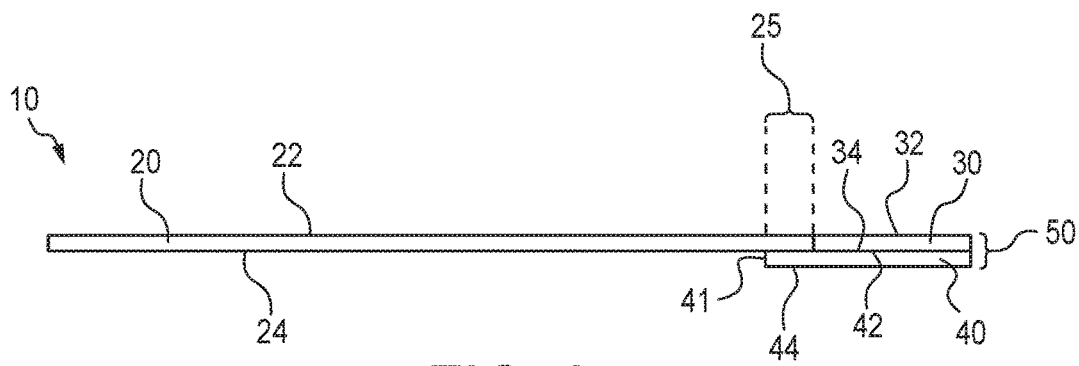
FIG. 2 is a schematic side elevational view of the closure assembly depicted in FIG. 1.
Figure 3:
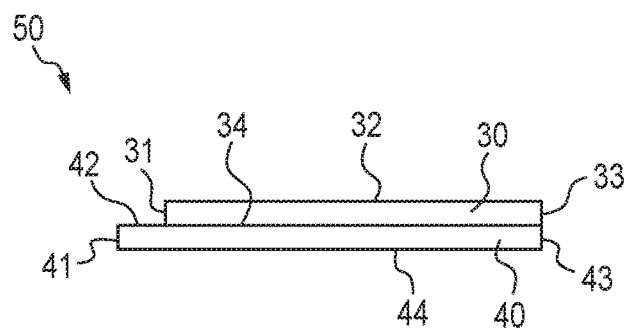
FIG. 3 is a schematic side elevational view of the extended fingerlift depicted in FIG. 1.

FIGS. 1-3 schematically illustrate a closure assembly 10 comprising a fastening tape carrier 20 and an extended fingerlift 50 secured thereto, in accordance with one embodiment of the present subject matter. The carrier 20 defines a proximal end 21, an opposite distal end 23, an outer face 22, and an oppositely directed underside 24. The proximal end 21 is typically attached to an absorbent article, and the distal end 23 is "free" or at least initially unattached. The outer face 22 is typically coated with a release agent, and the underside 24 may include one or more regions of adhesive. Specifically, in certain versions the underside 24 includes one or more regions of adhesive. And in other versions, the underside 24 is free of adhesive.

The extended fingerlift 50 comprises a fingerlift strip 30, a thin extension strip 40, and provisions for securing at least one of the fingerlift strip 30 and the extension strip 40 to the distal end 23 of the carrier 20.

The fingerlift strip 30 defines an outer face 32, an oppositely directed underside 34, a proximal end 31, and a distal end 33.

The extension strip 40 defines an outer face 42, an oppositely directed underside 44, a proximal end 41, and a distal end 43.

The terms "proximal" and "distal" correspond to those of the closure assembly and its components. Thus, the distal end of a closure assembly component such as the fingerlift strip or the extension strip, is the end closest to the distal end of the closure assembly upon attachment. And the proximal end of the closure assembly component is the end which is closest to the proximal end of the closure assembly upon attachment.

The fingerlift strip 30 and the extension strip 40 are positioned relative to one another to thereby define a receiving region for the distal end 23 of the carrier 20. Specifically, in many embodiments the receiving region is in the form of a ledge resulting from exposed portions of the outer face 42 of the extension strip 40 adjacent the proximal end 41 of the strip 40, and the generally transversely oriented distal end 31 of the fingerlift strip 30. The ledge shaped receiving region is described in greater detail herein.

The fingerlift strip 30 and the extension strip 40 are positioned and secured relative to one another such that at least a portion, and in many embodiments at least a majority portion, of the underside 34 of the fingerlift strip 30 is disposed upon and contacting at least a portion of the outer face 42 of the extension strip 40.

In addition, in many embodiments the length, i.e., the linear span between proximal and distal ends, of the extension strip 40 is greater than the length of the fingerlift strip 30. And in many embodiments, the width, i.e., the span transverse to length, of the extension strip 40 and the fingerlift strip 30 are equal or substantially so. However, it will be understood that the present subject matter includes embodiments in which the relative proportions of the extension strip and the fingerlift strip are different than described and/or shown herein.

In the particular embodiment of the extended fingerlift 50, the distal ends of the fingerlift strip 30 and the extension strip 40, i.e., ends 33 and 43, respectively, are flush or coextensive with one another or substantially so. The proximal ends of the fingerlift strip 30 and the extension strip 40, i.e., ends 31 and 41, respectively, are not flush and the proximal end 41 of the extension strip 40 extends beyond the proximal end 31 of the fingerlift strip 30, thereby resulting in the ledge shaped receiving region.

The fingerlift strip 30 and the extension strip 40 are secured to one another to form a one-piece, unitary component, i.e., the extended fingerlift 50. The fingerlift strip 30 and the extension strip 40 can be secured to one another by a variety of techniques including deposition of adhesive along at least a portion of the interface between their surfaces, lamination using heat and/or pressure, sealing techniques, and/or other means such as welding and more particularly ultrasonic welding. Specific examples of sealing techniques include ultrasonic sealing, and sealing with pressure and/or heat.

The extended fingerlifts of the present subject matter such as fingerlift 50 may also include provisions for securing the fingerlift 50 to the distal end 23 of a fastening tape carrier such as the carrier 20. Upon positioning the extended fingerlift 50 relative to the carrier 20 such that (i) the distal end 23 of the carrier 20 is directed toward and in certain embodiments contacting the proximal end 31 of the fingerlift strip 30, and (ii) a portion of the underside 24 of the carrier 20 is disposed on and in certain embodiments contacting a portion of the outer face 42 of the extension strip 40, a region of overlap 25 is defined. Generally, such positioning occurs upon placement of the distal end 23 within the receiving region of the extended fingerlift. In many embodiments, the securement provisions include material that bonds the carrier 20 with one or both of the fingerlift strip 30 and the extension strip 40. In certain embodiments, the provisions for securing an extended fingerlift to a carrier are in the form of one or more adhesives deposited along interface(s) of surfaces or regions of the components, and particularly along the region of overlap 25. Thus, for example and with reference to FIGS. 1-3, provisions for securing the extended fingerlift 50 to the distal end 23 of the carrier 20 include adhesive applied along one or both of (i) the interface between underside 24 and outer face 42 typically extending within the region of overlap 25, and (ii) the interface between distal end 23 and proximal end 31. However, it is contemplated that other strategies could be used to secure an extended fingerlift to a distal end of a carrier, such as adhesive-free techniques for example ultrasonic welding or lamination using heat and/or pressure applied to the various materials.

Upon securement of the extended fingerlift 50 to the carrier 20, the resulting closure assembly 10 is provided with a distal end region which can be readily identified by a user, particularly if the fingerlift strip 30 is colored or otherwise rendered conspicuous or visually striking. In addition, cost savings may be realized depending upon the relative costs of the materials of the carrier and the extended fingerlift. Specifically, lesser amounts of carrier material are required due to increases in overall length of a closure assembly upon securement of an extended fingerlift to a carrier. Additional details of extended fingerlifts and closure assemblies utilizing such are described in greater detail herein.

Figure 4:
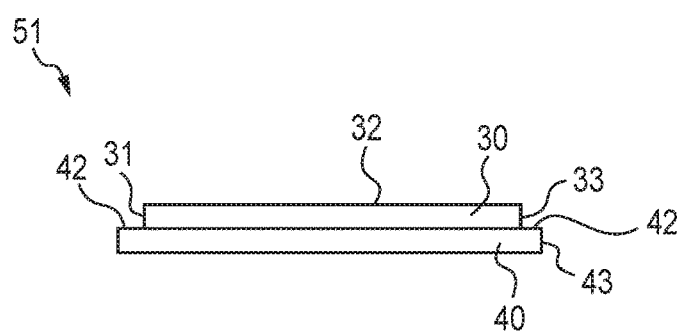
FIG. 4 is a schematic side elevational view of another embodiment of an extended fingerlift in accordance with the present subject matter.

FIG. 4 is a schematic side view of another embodiment of an extended fingerlift 51 in accordance with the present subject matter. In this version, the fingerlift 51 utilizes relative positioning of the fingerlift strip 30 and the extension strip 40 such that their distal ends 33 and 43, respectively, are not flush. More particularly, the ends 33 and 43 are positioned so that the end 43 extends beyond the end 33 to thereby expose a portion of the outer face 42 adjacent to the distal end 33.

Figure 5:
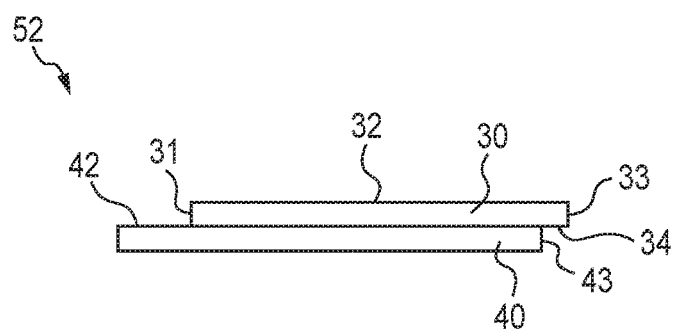
FIG. 5 is a schematic side elevational view of another embodiment of an extended fingerlift in accordance with the present subject matter.

FIG. 5 is a schematic side view of another embodiment of an extended fingerlift 52 in accordance with the present subject matter. In this version, the fingerlift 52 utilizes relative positioning of the fingerlift strip 30 and the extension strip 40 such that their distal ends 33 and 43, respectively, are not flush. More particularly, the ends 33 and 43 are positioned so that the end 33 extends beyond the end 43 to thereby expose a portion of the underside 34 adjacent to the distal end 43.

Figure 6:
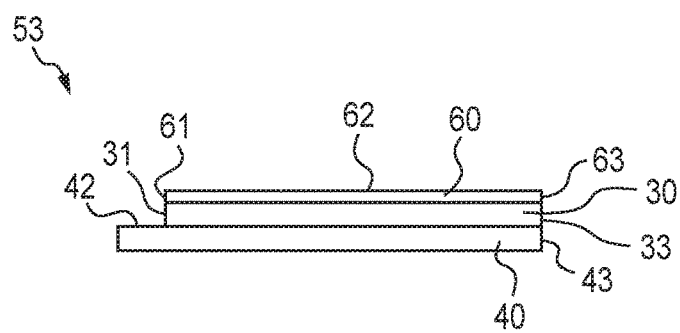
FIG. 6 is a schematic side elevational view of another embodiment of an extended fingerlift in accordance with the present subject matter.

FIG. 6 is a schematic side view of another embodiment of an extended fingerlift 53 in accordance with the present subject matter. In this version, the fingerlift 53 comprises one or more layers or materials disposed on the fingerlift strip 30, collectively shown as 60. The layer(s) 60 define an outer face 62 extending between a proximal end 61 and a distal end 63. The proximal end 61 may or may not be flush with the end 31. And, the distal end 63 may or may not be flush with one or both ends 33 and 43. In certain versions, the layer 60 is a release layer or a release coating. Thus, in many of the embodiments described herein, the outer face 32 of the fingerlift strip 30 can include one or more release layers or release coatings disposed thereon. In certain versions, the fingerlift strip includes one or more release materials disposed on at least a portion of the outer face of the fingerlift strip.

Figure 7:
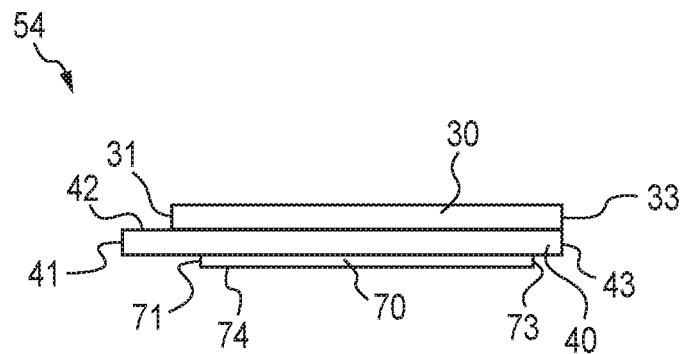
FIG. 7 is a schematic side elevational view of another embodiment of an extended fingerlift in accordance with the present subject matter.

FIG. 7 is a schematic side view of another embodiment of an extended fingerlift 54 in accordance with the present subject matter. In this version, the fingerlift 54 comprises one or more layers or materials disposed along the extension strip 40, collectively shown as 70. The layer(s) 70 define an underside 74 extending between a proximal end 71 and a distal end 73. The proximal end 71 may or may not be flush with the ends 31 and/or 41. And, the distal end 73 may or may not be flush with one or both ends 33 and 43.

Figure 8:
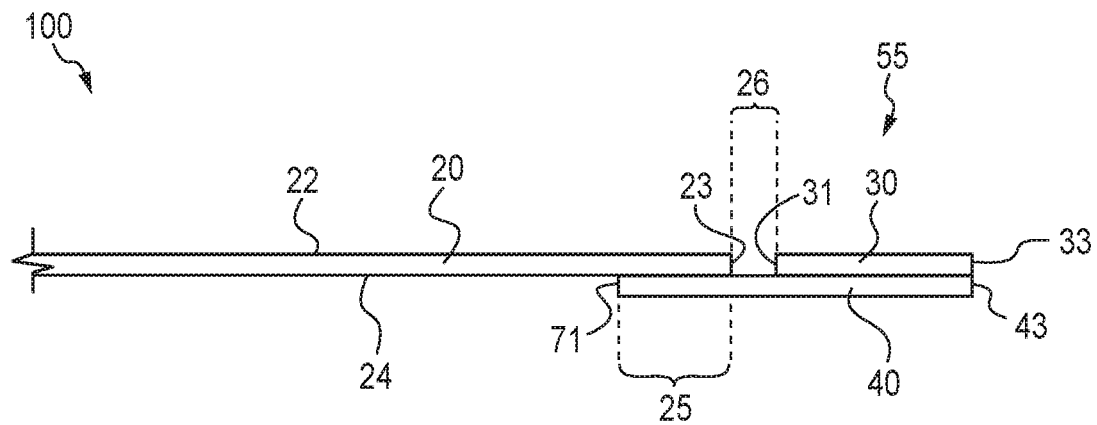
FIG. 8 is a schematic side elevational view of another embodiment of a closure assembly including an extended fingerlift in accordance with the present subject matter.

FIG. 8 is a schematic side elevational view of another closure assembly 100 in accordance with the present subject matter. The closure assembly 100 comprises the previously noted fastening tape carrier 20 and another version of an extended fingerlift 55. The previously noted region of overlap 25 is depicted. The carrier 20 and the extended fingerlift 55 are secured to one another such that the distal end 23 of the carrier 20 is spaced from and does not contact, a proximal end 31 of the fingerlift strip 30 of the extended fingerlift 55. In this embodiment, a spaced region 26 is defined between the ends 23 and 31.

Figure 9:
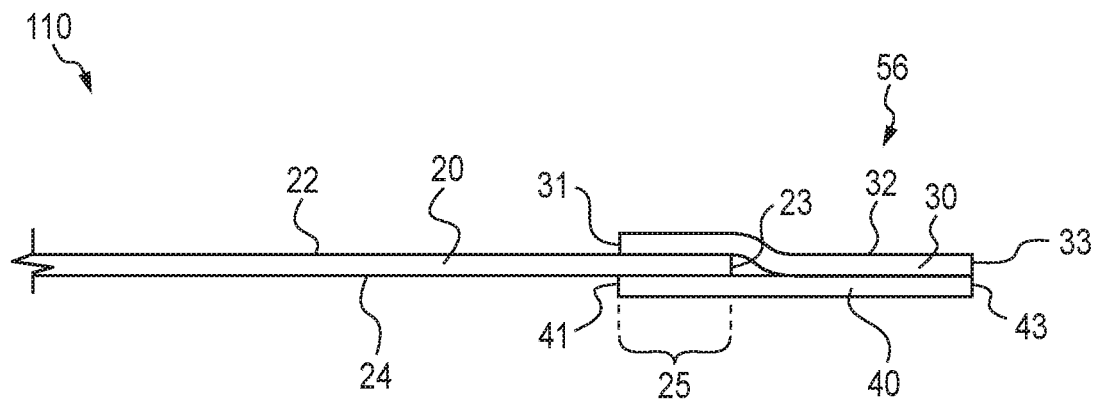
FIG. 9 is a schematic side elevational view of another embodiment of a closure assembly including an extended fingerlift in accordance with the present subject matter.

FIG. 9 is a schematic side elevational view of another closure assembly 110 in accordance with the present subject matter. The closure assembly 110 comprises the previously noted fastening tape carrier 20 and another version of an extended fingerlift 56. The carrier 20 and the extended fingerlift 56 are secured to one another such that the distal end 23 of the carrier 20 is disposed between and contacting proximal end regions adjacent ends 31, 41 of the fingerlift strip 30 and the extension strip 40. The distal end 23 of the carrier can extend along the proximal end regions of the strips 30, 40 for a distance corresponding to the previously noted region of overlap 25.

Figure 10:
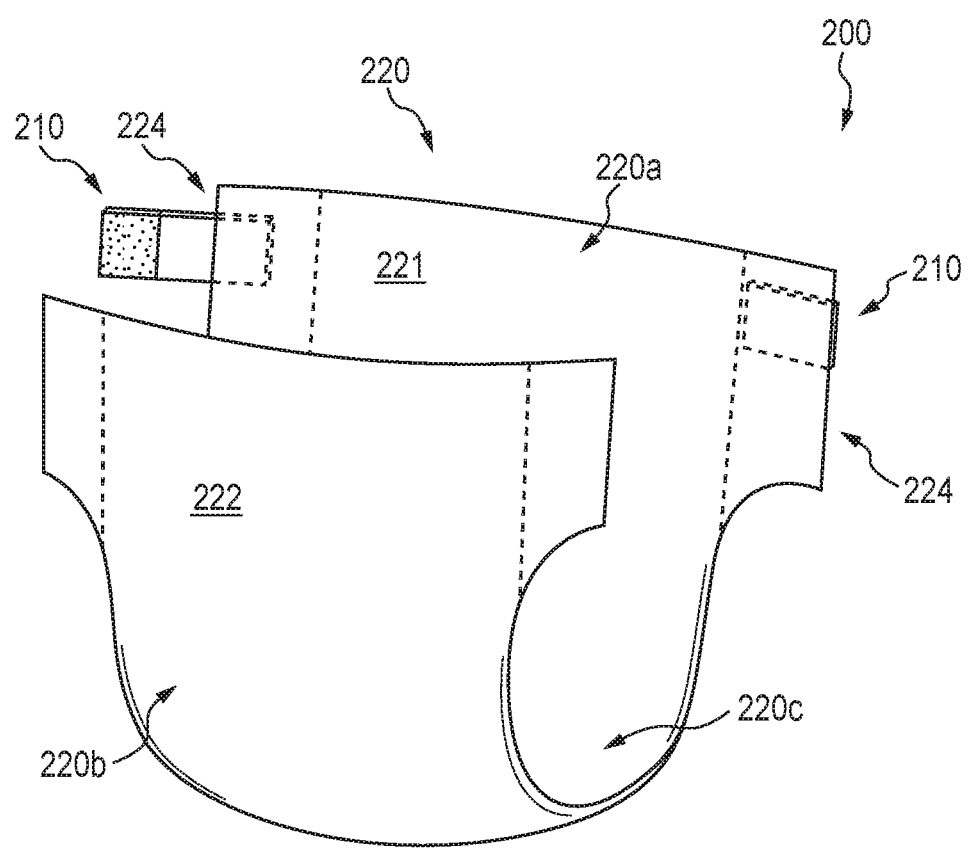
FIG. 10 is a schematic perspective view of an absorbent article including two closure assemblies in accordance with the present subject matter.

FIG. 10 illustrates a disposable absorbent article 200, e.g., a baby diaper, including a pair of closure assemblies 210 joined to a diaper chassis 220. Notably, the left closure assembly 210 is shown in an installed and deployed condition, while the right closure assembly 210 is shown in an installed but un-deployed condition. In practice, the illustrated diaper chassis 220 is constructed of a liquid absorbent core (not shown) enclosed between a liquid permeable topsheet 221 (which generally forms an inner surface of the diaper located adjacent a wearer when the diaper is worn) and a liquid impermeable backsheet 222 (which generally forms an outer surface of the diaper when worn). The diaper chassis 220 generally includes a rear portion 220a intended to cover a wear's behind, a front portion 220b intended to cover a wear's front and a crotch portion 220c therebetween.

In the illustrated embodiment, the two closure assemblies 210 are joined to the rear portion 220a of the diaper chassis 220 along opposing side ends or edges 224 thereof. As shown, the closure assemblies 210 may be joined directly to the diaper chassis 220, or alternately, via intervening side panels (not shown) which may be elastic or inelastic. The closure assemblies 210 allow each side of the rear portion 220a of the diaper chassis 220 to be releasably attached to the front portion 220b of the diaper chassis 220 thereby selectively forming a waistband around a wearer.

Suitably, no landing strip or separate layer of loop material is provided for receiving the closure assemblies 210 on the front portion 220b of the diaper chassis 220. Rather the closure assemblies 210 selectively engage with and/or releasably attach directly to the backsheet 222 forming the outer surface of the front portion 220b of the diaper chassis 220. However, it will be appreciated that the present subject matter includes a wide array of configurations of absorbent articles. For example, the present subject matter includes embodiments of absorbent articles which include one or more landing strips (not shown in FIG. 10) that receive a corresponding closure assembly. Thus, it will be understood that the various extended fingerlifts and closure assemblies using such extended fingerlifts can be utilized in conjunction with absorbent articles that are free of landing strips, or instead which include landing strips or other designated receiving regions or loop material(s).

In practice, the backsheet 222 may be suitably formed from an appropriate nonwoven material. In one suitable embodiment, the backsheet 222 is formed from a spunbond nonwoven material having a weight in the range of approximately 10 gsm to approximately 25 gsm (grams per square meter), particularly in the range of approximately 12 gsm to approximately 20 gsm, more particularly in the range of approximately 12 gsm to approximately 18 gsm. The nonwoven material suitably includes an entangled or otherwise arranged collection of fibers or filaments that may be thermally bonded or adhesively bonded to a polymer web or backing (e.g., a polyethylene backing). Of course, alternately, other known nonwoven materials may be similarly used and/or other known methods for manufacturing the nonwoven material may be employed.

It will be understood that the present subject matter includes a wide array of absorbent articles and is not limited to diapers. Instead, the various embodiments of extended fingerlifts and closure assemblies using such can be incorporated in, and/or used in association with, a wide array of absorbent articles besides diapers.

Additional details of the extended fingerlifts and closure assemblies are described as follows.

Extension Strips

The extension strip, such as strip 40 can be made of cloth, kraft paper, cellophane film, nonwoven webs, polymeric films, e.g., filmic materials such as polypropylene, polyethylene terephthalate, and polyethylene, or other suitable materials or laminates. In particular embodiments of the present subject matter, the extension strip is polypropylene and more particularly an oriented polypropylene, and more particularly a biaxially oriented polypropylene (BOPP). Combinations of materials are also contemplated. The non-adhesive side(s) of the extension strip can include release coatings (e.g., a silicone coating, a carbamate coating, etc.) if such is desirable, e.g., to prevent blocking issues during assembly, storing, and/or dispensing of the extended fingerlift and/or the closure assembly for installation. If the extension strip is to be elastic, substrate selection could include extruded or coextruded elastic films that are monolayers or that include suitable skins, backings, or release linings.

Fingerlift Strips

The fingerlift strip, such as strip 30 can be made of cloth, kraft paper, cellophane film, nonwoven webs, polymeric films, e.g., filmic materials such as polypropylene, polyethylene terephthalate, and polyethylene, or other suitable materials or laminates. In many embodiments, the fingerlift strips include one or both of a filmic material and/or a nonwoven material. As previously noted, it may be beneficial or desirable to color the fingerlift strip. Combinations of materials for the fingerlift strips are also contemplated. The non-adhesive side(s) of the fingerlift strips can include release coatings (e.g., a silicone coating, a carbamate coating, etc.) if such is desirable, e.g., to prevent blocking issues during assembly, storing, and/or dispensing of the extended fingerlift and/or the closure assembly for installation.

In particular embodiments, the distal ends of the fingerlifts and/or the distal ends of either or both of the fingerlift strip and the extension strip may be in the form of a serrated or wavy edge for example. This configuration promotes separation from adjacent regions of the closure assembly when the closure assembly is in its stored position. In addition, a serrated or wavy configuration may provide an aesthetically pleasing appearance. The appearance of the distal end can be further altered and/or improved by utilizing a finger lift that is colored, for example blue or pink. Providing a colored or visually accentuated finger lift also serves to aid in identifying the location of the distal end of the carrier and/or fingerlift upon attachment to the landing zone or other diaper area. The finger lift can be provided in a wide array of shapes, sizes, and configurations.

As previously noted, the fingerlifts can be colored or otherwise rendered more visually pronounced. In many embodiments, this is performed by incorporating one or more inks, dyes, pigments, or other like agents or combinations thereof into the material(s) of the fingerlift strip.

Closure Assemblies Using Extended Fingerlifts

As previously noted, the closure assemblies of the present subject matter include a fastening tape carrier, such as carrier 20. The carrier can be made of cloth, kraft paper, cellophane film, nonwoven webs, polymeric films or other suitable materials or laminates. The term "laminates" as used herein refers to a wide array of materials and combinations of materials. For example, the term laminates includes but is not limited to polymer webs, nonwoven webs, combinations of polymeric webs and nonwoven webs, and various extrusion laminated products. For example, in forming an extrusion laminated product, a nonwoven material is fed to the nip of cooling rolls for a film extrusion product. The extruded product and nonwoven material are intimately bonded together, to thereby form an extrusion laminated product. The carrier may be nonextensible and formed of conventional polymers such as polypropylene, polyvinyl chloride, polyethylene terephthalate, and polyethylene film. In another embodiment, the carrier is extensible. Extensible films include extensible non-woven and woven fabric and polymeric films, such as those described in U.S. Pat. No. 6,669,887. It will be appreciated that in no way is the subject matter limited to these materials. In many embodiments, a release material or coating is provided on a back side surface, i.e. surface 22, of the carrier. For example, a silicone or carbamate coating may be applied to the back side surface to promote deployment of the closure assembly.

For embodiments in which an adhesive layer is applied along an underside such as underside 24, the adhesive is typically an adhesive having a peel strength that is sufficient to securely and in many embodiments, permanently attach the carrier to the outer surface of the absorbent article. The adhesive used may be any conventional adhesive, including pressure sensitive adhesives and non-pressure sensitive adhesives. Suitable pressure sensitive adhesives include acrylic resin and natural or synthetic based rubber adhesives. In one embodiment, the adhesive is a hot melt pressure sensitive adhesive of the A-B-A block copolymer type comprising an elastomeric B-block derived from isoprene and thermoplastic A-blocks derived from styrene as disclosed in U.S. Pat. No. 3,932,328. Illustrative rubber based adhesives include styrene-isoprene-styrene, styrene-butadiene-styrene, styrene-ethylene/butylenes-styrene and styrene-ethylene/propylene-styrene that may optionally contain diblock components such as styrene isoprene and styrene butadiene. The adhesive layer may be applied using hot-melt, solvent or emulsion techniques. It will be appreciated that in no way is the subject matter limited to these materials. The adhesive layer can be continuous, or discontinuous and/or pattern coated such as described in US 2014/0010984.

The closure assemblies can also utilize one or more mechanical closure elements such as hook and loop fastener elements which are also known in the art as Velcro fasteners. For example, a carrier such as carrier 20 can include one or more regions of a plurality of hook members and/or a plurality of loop members. Materials providing hook and loop members are well known in the art. And, a wide array of configurations and constructions are known for hooks and loops. For example, extensive information pertaining to hook and loop members and materials is set forth in U.S. Pat. Nos. 5,053,028; 5,176,670; 5,860,964; 6,146,369; and 6,524,294.

The closure assemblies can also include adhesive regions in combination with mechanical closure elements.

The various regions of adhesive and/or mechanical closure elements can be provided on one or both faces of the carrier, for example on either or both of the outer face and the underside of the carrier 20.

For embodiments of closure assemblies that include an adhesive layer and optionally in further combination with one or more mechanical closure elements along an underside of a carrier, one or more regions or layers of a release agent are applied along the oppositely directed face, i.e., the outer face of the carrier.

It is also contemplated that one or more elastic regions can be provided in the closure assemblies. The elastic regions can be provided by incorporation of materials exhibiting elastic properties. The elastic regions can also be provided by forming or providing certain structural features into the closure assemblies. The elastic regions can also be provided by performing one or more processing operations upon desired regions of the closure assemblies. Details as to forming and/or providing elastic regions in closure assemblies closure assemblies are provided in U.S. Pat. Nos. 5,057,097; 6,645,338; 6,221,483; 5,690,628; 6,524,294; and 5,720,739 all assigned to Avery Dennison Corporation.

Securement Provisions

The securement provisions are typically in the form of adhesive which is disposed along contacting surfaces of one or both of the distal end or end region of the carrier, such as carrier 20; and the receiving region of the fingerlift such as any of fingerlifts 50-56 for example. The adhesive can be any adhesive suitable for the end use application, and particularly includes any of the adhesives previously described herein with regard to the closure assemblies. Although adhesive is used for the securement provisions, the present subject matter includes other provisions such as laminating by heat and/or pressure, other sealing means, and by welding for example by ultrasonic welding.

Methods

The present subject matter also provides methods of facilitating or promoting identification or visually recognizing, and grasping, a fastening member of a closure assembly such as used in absorbent articles. The methods generally comprise providing closure assemblies and extended fingerlifts as described herein. The methods also comprise positioning a distal end of a fastening tape carrier or strip of a closure assembly in a receiving region of an extended fingerlift. After such positioning, the distal end of the carrier strip and the extended fingerlift are secured to one another. Securing can be performed using a variety of techniques such as but not limited to the use of adhesive along at least portions of adjoining surfaces, application of heat and pressure such as during lamination, and by welding operations such as ultrasonic welding. The methods can also include incorporating one or more coloring agents into the fingerlift strip of the extended fingerlift.

Applications and Articles

Figure 11:
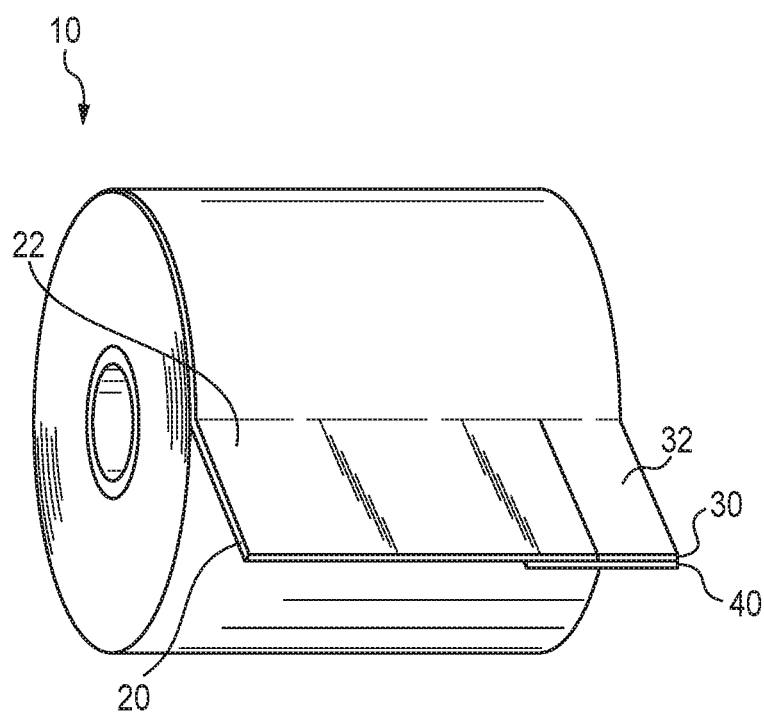
FIG. 11 is a schematic perspective view of the closure assembly depicted in FIGS. 1-3 in a roll or spool form.

The closure assemblies and the fingerlifts can be provided in separate rolled configurations, or in many embodiments, engaged to one another as shown in FIG. 1 and then provided in a roll form. In many embodiments, the closure assemblies and the extended fingerlifts are joined and secured to one another, and the resulting combination provided in a roll or spool, such as depicted in FIG. 11. The width of the roll of closure tape of the present subject matter depends on the intended application. Typically, the rolls that are used for closure assemblies for disposable articles have a width in the range of about 30 to about 140 mm. In one embodiment, the width of the rolls is in the range of about 45 to about 75 mm. The closure tape can be provided in a roll, for example, as a disc wound roll or a spool wound roll. The closure assemblies of the subject matter can be cut from a stock roll. In use, a segment of the roll of composite closure tape is cut from the roll in a desired length.

The present subject matter can be utilized in an assortment of articles and particularly absorbent articles for example personal care absorbent articles. Nonlimiting examples of such articles include infant and toddler diapers, adult diapers, feminine hygiene articles, disposable absorbent articles, and related packaging and tapes.

Additional Alternate Embodiments

Figure 12:
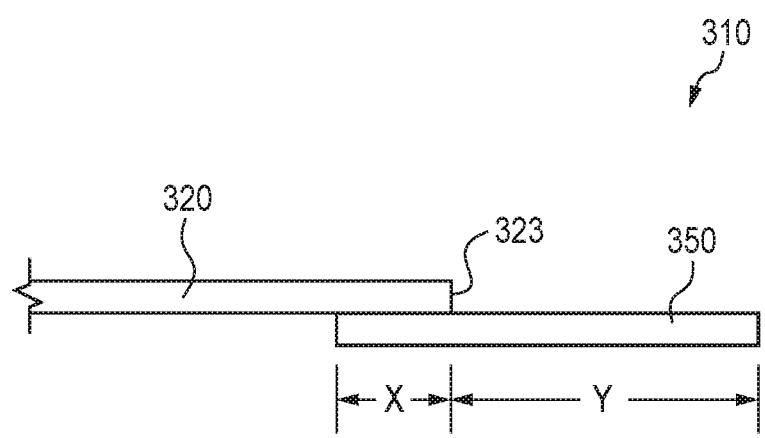
FIG. 12 is a schematic side elevational view of an alternate embodiment of a closure assembly in accordance with the present subject matter.

The present subject matter includes a wide array of variant designs and configurations of fingerlifts and/or closure assemblies. For example, closure assemblies that include an extension member, a distal projection, or end component which is attached to a distal end of a carrier strip are included in the present subject matter. Although it is generally known to attach sections of material to carrier strips to facilitate identification, the present subject matter provides constructions in which the portion of the section of material which extends beyond the distal end of the carrier strip, extends significantly beyond the distal end of the carrier strip, for example at least 2 mm, particularly at least 5 mm, and more particularly at least 10 mm; and up to a maximum extension distance of about 50 mm. In a particular embodiment, an extension distance of 13 mm is used. FIG. 12 schematically depicts an alternate embodiment closure assembly 310 comprising a carrier strip 320 defining a distal end 323, and an extension member 350 attached to the carrier strip 320 and extending beyond the distal end 323 of the strip 320. The previously noted extension distances are depicted as dimension Y in FIG. 12.

The present subject matter also provides constructions in which a ratio of the dimensions of extension and overlap of the section of material attached to the distal end of the carrier strip range from about 25:1 to about 2:1, and more particularly from 10:1 to 3:1, respectively. Referring to FIG. 12, the dimension of extension of the extension member 350 is shown as dimension Y, and the dimension of overlap of the extension member 350 is shown as dimension X. Thus, the previously noted ratio Y/X is within the range of about 25:1 to about 3:1, and particularly 10:1 to 3:1. In a particular embodiment, an overlap distance of 3 mm is used. A construction using that overlap distance and an extension distance of 13 mm results in a ratio Y/X of about 4.3.

All of the previously noted details and materials of the extended fingerlift(s) are applicable to the noted extension member 350. And all of the previously noted details and materials of the fastening tape carrier are applicable to the noted carrier strip 320.

Many other benefits will no doubt become apparent from future application and development of this technology.

All patents, applications, standards, and articles noted herein are hereby incorporated by reference in their entirety.

The present subject matter includes all operable combinations of features and aspects described herein. Thus, for example if one feature is described in association with an embodiment and another feature is described in association with another embodiment, it will be understood that the present subject matter includes embodiments having a combination of these features.

As described hereinabove, the present subject matter solves many problems associated with previous strategies, systems and/or devices. However, it will be appreciated that various changes in the details, materials and arrangements of components, which have been herein described and illustrated in order to explain the nature of the present subject matter, may be made by those skilled in the art without departing from the principle and scope of the claimed subject matter, as expressed in the appended claims.

What is claimed is:

1. An extended fingerlift configured for securement at a distal end of a fastening tape carrier of a closure assembly, the extended fingerlift comprising:
    an extension strip defining a proximal end, a distal end, an outer face and an oppositely directed underside;
    a fingerlift strip defining a proximal end, a distal end, an outer face and an oppositely directed underside;
    wherein the extension strip and the fingerlift strip are positioned relative to one another to thereby define a receiving region for receipt of the distal end of the fastening tape carrier;
    wherein the extended fingerlift is secured to the distal end of the fastening tape carrier;
    wherein the proximal ends of the fingerlift strip and the extension strip are not flush;
    wherein the receiving region is in the form of a ledge comprising a portion of the outer face of the extension strip adjacent the proximal end of the extension strip; and
    wherein a portion of the distal end of the fastening tape carrier is disposed on a portion of the outer face of the extension strip within the receiving region.

2. The extended fingerlift of claim 1 wherein the extension strip and the fingerlift strip are secured to each other.

3. The extended fingerlift of claim 2 wherein the extension strip and the fingerlift strip are secured to each other by use of adhesive.

4. The extended fingerlift of claim 1 wherein the distal end of the extension strip and the distal end of the fingerlift strip are flush and coextensive with one another.

5. The extended fingerlift of claim 1 wherein at least a portion of the outer face of the extension strip contacts the underside of the fingerlift strip.

6. The extended fingerlift of claim 1 wherein the width of the extension strip is equal or substantially so, to the width of the fingerlift strip.

7. The extended fingerlift of claim 1 wherein the fingerlift strip includes a material selected from the group consisting of (i) a filmic material, (ii) a nonwoven material, and (iii) combinations thereof.

8. The extended fingerlift of claim 1 wherein the extension strip includes a material selected from the group consisting of (i) a filmic material, (ii) a nonwoven material, and (iii) combinations thereof.

9. The extended fingerlift of claim 8 wherein the extension strip includes a filmic material.

10. The extended fingerlift of claim 9 wherein the filmic material is polypropylene.

11. The extended fingerlift of claim 10 wherein the polypropylene is oriented.

12. The extended fingerlift of claim 11 wherein the oriented polypropylene is biaxially oriented.

13. The extended fingerlift of claim 1 wherein the fingerlift strip includes at least one coloring agent selected from the group consisting of (i) inks, (ii) dyes, (iii) pigments, and (iv) combinations thereof.

14. The extended fingerlift of claim 1 wherein the fingerlift strip includes at least one layer or region of a release material.

15. The extended fingerlift of claim 14 wherein the release material is disposed on the outer face of the fingerlift strip.

16. A closure assembly configured for incorporation and use in an absorbent article, the closure assembly comprising the extended fingerlift of claim 1.

17. The closure assembly of claim 16 wherein the distal end of the fastening tape carrier is secured to the extended fingerlift by adhesive in the receiving region defined by the extended fingerlift.

18. The closure assembly of claim 16 wherein the closure assembly is in a roll or spool form.

19. The closure assembly of claim 18 wherein the fingerlift strip includes a release material disposed on at least a portion of the outer face of the fingerlift strip.

* * * * *